(12) United States Patent
Karger et al.

(10) Patent No.: US 6,660,149 B1
(45) Date of Patent: Dec. 9, 2003

(54) MULTICHANNEL MICROSCALE SYSTEM FOR HIGH THROUGHPUT PREPARATIVE SEPARATION WITH COMPREHENSIVE COLLECTION AND ANALYSIS

(75) Inventors: Barry L. Karger, Newton, MA (US); Lev Kotler, Brighton, MA (US); Frantisek Foret, Malden, MA (US); Marek Minarik, Winthrop, MA (US); Karel Kleparnik, Brno (CZ)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 09/530,118

(22) PCT Filed: Oct. 23, 1998

(86) PCT No.: PCT/US98/22522

§ 371 (c)(1),
(2), (4) Date: Apr. 24, 2000

(87) PCT Pub. No.: WO99/22228

PCT Pub. Date: May 6, 1999

Related U.S. Application Data

(60) Provisional application No. 60/062,787, filed on Oct. 24, 1997.

(51) Int. Cl.[7] .................. G01N 27/26; G01N 27/44
(52) U.S. Cl. ............... 204/601; 204/451; 204/452; 204/603
(58) Field of Search ................. 204/450, 451, 204/452, 453, 454, 455, 600, 601, 602, 603, 604, 605

(56) References Cited

U.S. PATENT DOCUMENTS

| | | | |
|---|---|---|---|
| 4,716,101 A | 12/1987 | Thompson et al. | ............ 435/4 |
| 5,541,420 A | * 7/1996 | Kambara | .................... 204/602 |

OTHER PUBLICATIONS

Wolfgang Weinmann et al., Capillary electrophoresis–maxtrix–assisted laser–desorption ionization mass spectrometry of proteins Journal of Chromatography A, 680 pp. 353–361, 1994.*

Hollis J. Boss et al. "Multiple Sequential Fraction Collection of Peptides and Glycopeptides by High–Performance Capillary Electrophoresis" Analytical Biochemistry 230 pp. 123–129, 1995.*

Takashi Irie et al., "Automated DNA Fragment Collection by Capillary Array Gel Electrophoresis in Search of Differentially Expressed Genes", Electrophoresis 21:367–374, (2000).

* cited by examiner

*Primary Examiner*—Nam Nguyen
*Assistant Examiner*—John S. Starsiak, Jr.
(74) *Attorney, Agent, or Firm*—William H. May; D. David Hill; Weingarten, Schurgin, Gagnebin & Lebovici LLP

(57) ABSTRACT

A modular multiple lane or capillary electrophoresis (chromatography) system that permits automated parallel separation and comprehensive collection of all fractions from samples in all lanes or columns, with the option of further on-line automated sample fraction analysis, is disclosed. Preferably, fractions are collected in a multi-well fraction collection unit, or plate (40). The multi-well collection plate (40) is preferably made of a solvent permeable gel, most preferably a hydrophilic, polymeric gel such as agarose or cross-linked polyacrylamide.

9 Claims, 12 Drawing Sheets

Drilling the mold

Casting the silicon rubber

Silicon negative

Casting the polymer solution

Gel plate

Fig. 9A  Original 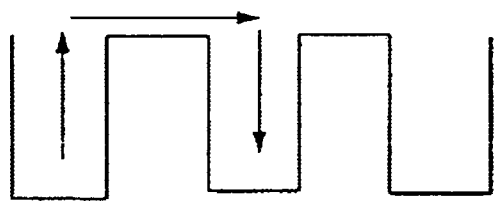
Fig. 9B  "Nozzle" 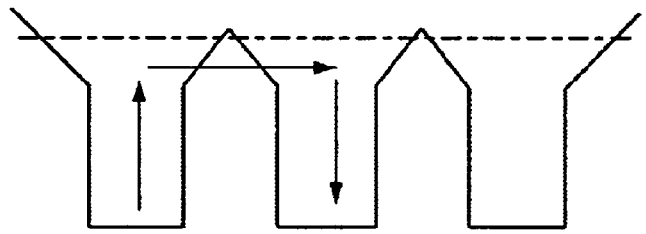

MULTICHANNEL MICROSCALE SYSTEM FOR HIGH THROUGHPUT PREPARATIVE SEPARATION WITH COMPREHENSIVE COLLECTION AND ANALYSIS

CROSS REFERENCE TO RELATED APPLICATIONS

This application claims priority from U.S. Provisional Patent Application No. 60/062787, filed Oct. 24, 1997, the whole of which is hereby incorporated by reference herein.

STATEMENT REGARDING FEDERALLY SPONSORED RESEARCH OR DEVELOPMENT

Part of the work leading to this invention was carried out with United States Government support provided under a grant from the Department of Energy, Grant No. DE-FG02-90ER60985. Therefore, the U.S. Government has certain rights in this invention.

BACKGROUND OF THE INVENTION

Following the use of most modern separation techniques, further treatment of the separated components of a sample is required to obtain more complete information about the nature of the components. For example, methods of functional genomics (e.g., differential display (Liang et al., Science 257:967–971, 1992), AFLP (Vos et al., Nucl. Acid Res. 23:4407–4414, 1995), etc.) produce a pattern of separated DNA fragments, but the products of differentially expressed genes have to be identified separately. As another example, methods to discriminate mutations such as constant denaturant capillary electrophoresis (CDCE) also require subsequent determination of the specific mutation (Khrapko et al., Nucl. Acid Res. 22:364–369, 1994). To perform such a multidimensional analysis, a high throughput preparative separation system capable of collecting comprehensively all components of the sample mixture would be desirable.

Current micropreparative techniques for purification and fraction collection generally use either chromatography or electrophoresis for separation of the sample components. Fully automated single column systems are available, allowing fractionation and collection of specific sample components per run (Karger et al., U.S. Pat. No. 5,571,398 (1996); Carson et al., U.S. Pat. No. 5,126,025 (1992)). When fractions from multiple lanes are required, e.g., of DNA fragments, slab gel electrophoresis can be used for the simultaneous separation of the samples, followed by manual recovery of the desired fractions from the gel. This process is slow, labor intensive and imprecise. In another analytical approach, DNA fragments can be collected onto a membrane using direct transfer electrophoresis (Richterich et al., Meth. Enzymol. 218:187–222 1993). However, recovery of the samples from the membrane is slow and difficult.

BRIEF SUMMARY OF THE INVENTION

The invention is directed to a modular multiple lane or capillary electrophoresis (chromatography) system that permits automated parallel separation and comprehensive collection of all fractions from samples in all lanes or columns, with the option of further on-line automated sample analysis of sample fractions. At its most basic, the system includes a separation unit such as a capillary column having each end immersed in a buffer solution, the inlet end being immersed in a regular buffer tank and the outlet end being in connection with the appropriate multi-well collection device. The outlet end may also be connected to a sheath flow generator. The capillary column, which may or may not have an inner coating and may be open tube or filled with any of a variety of different separation matrices, is used for separation of mixtures of compounds using any desired separation technique. The term "capillary column" is meant to include a vessel of any shape in which a microseparation technique can be carried out. For example, other types of separation units, such as channels in a microchip or other microfabricated device, are also contemplated.

Depending on the separation method chosen, a sample mixture could be introduced into one or more separation lanes simultaneously, using an electric field, or pressure, vacuum, or gravitational forces. Fractions usually are collected regardless of the sample composition in fixed time intervals, preferably every few seconds, into, e.g., a multi-well plate with fixed well volume, preferably, e.g., 0.5–10 microliter or smaller. The multi-well plate has sufficient capacity to collect all possible fractions during a separation run. Determination of sample separation profile (s) is accomplished by monitoring, e.g., an optical characteristic of the sample components, for example, laser induced fluorescence, color, light absorption (UV, visible or IR), using on-column or on-lane detection. After the run is completed, the desired fractions are selected using sample profiles recorded during the separation experiment. Determination of sample separation profile and selection of fractions may also be achieved in a post-process procedure, where collected fractions are scanned in a separate optical device capable of registering a desired optical characteristic of the collected material. Fractions of interest are transferred to microtubes or standard microtiter plates for further treatment.

The multi-well fraction collection unit, or plate, is preferably made of a solvent permeable gel, most preferably a hydrophilic, polymeric gel such as agarose or cross-linked polyacrylamide. A polymeric gel generally useful in the system of the invention is an entangled or cross-linked polymeric network interpenetrated by a suitable solvent so that the final composition has the required physico-chemical properties, e.g., sufficient electric conductivity (for, e.g., CE systems), rigidity and dimensional and chemical stability, to serve as the collection unit of the system of the invention. The polymer may or may not be cross-linked and may be linear or branched. Examples of suitable materials include, e.g., agarose, polyacrylamide, polyvinylpyrrolidone, polyethyleneglycol or polyvinylalcohol, and copolymers or combinations thereof. Other suitable materials for a collection unit include electrically conductive plastic or assemblies of micelles. The pore size(s) of gel network pores can be established as appropriate by modulating parameters such as polymer type, concentration, cross-linking agents and polymerization conditions.

BRIEF DESCRIPTION OF THE SEVERAL VIEWS OF THE DRAWING

Other features and advantages of the invention will be apparent from the following description of the preferred embodiments thereof and from the claims, taken in conjunction with the accompanying drawings, in which:

FIGS. 9A and 9B show two alternative configurations of individual wells of a multi-well collection unit in the micropreparative fraction collection system of the invention;

DETAILED DESCRIPTION OF THE INVENTION

The system of the invention will now be described in detail using as an example a system for the separation of fluorescently labeled DNA fragments by capillary electrophoresis; however, such a system can be applied to different sample materials, e.g., proteins, other biopolymers, and low molecular weight compounds, or can incorporate other separation methods, as well. Any method of separation could be employed, including but not limited to capillary electrophoresis (CE), capillary isoelectric focusing (CIEF), capillary electrochromatography (CEC) and capillary liquid chromatography (CLC). Furthermore, any detection parameter would be useful in the method of the invention, such as, e.g., laser induced fluorescence, color, light absorption (UV, visible or IR), radioactivity or conductivity.

Figure 1A:
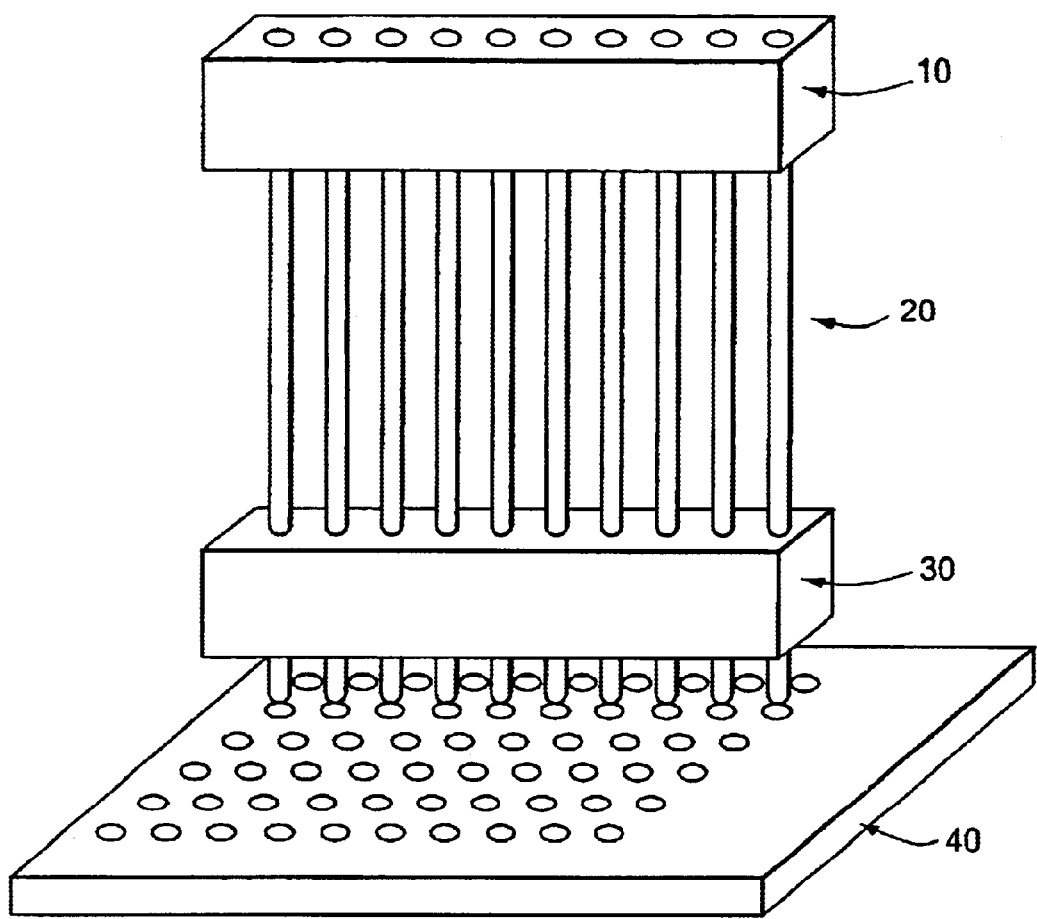
FIG. 1a shows one embodiment of the micropreparative fraction collection system of the invention.
Figure 1B:
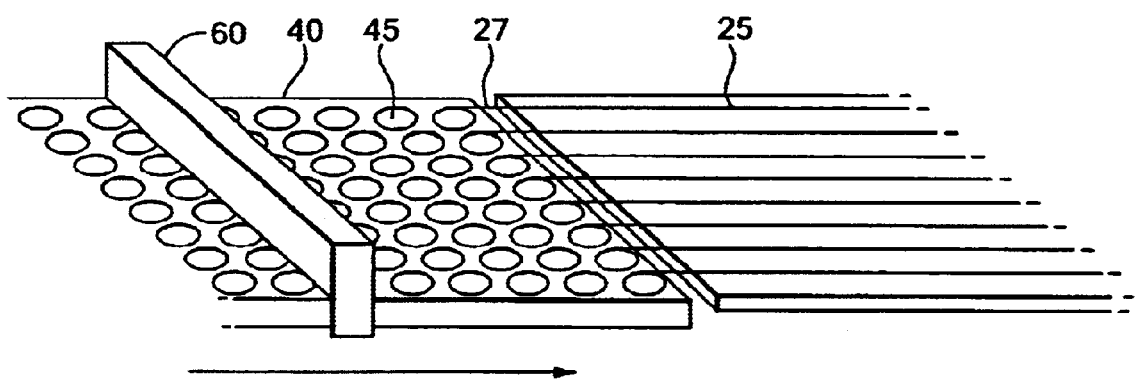
FIG. 1b shows an alternative embodiment of the micropreparative fraction collection system of the invention.

A basic micropreparative fraction collection system consists of the following main sections, as shown in FIG. 1a: a sample application unit (10), a separation unit of parallel capillary columns (20), a detection unit (30) and a multi-well fraction collection unit (40). In the orientation shown, i.e., with the capillaries positioned vertically, the system is most suitable for CLC analysis. For DNA fragments, separation can be performed using, e.g., fused silica capillaries filled with a separation matrix, e.g., agarose or linear polyacrylamide solution. As shown in FIG. 1b, separation can also be carried out in channels (25) in microfabricated chins. Such channels preferably would terminate in small tips (27) for ease of transfer of individual fractions to the multi-well fraction collection unit. Referring again to FIG. 1a, the DNA samples are injected in parallel from the sample application unit (10) at the cathode side of the separation unit (20), separated in the separation unit and collected at the anode side of the separation unit into the fraction collection unit (40). The collection period is determined depending on the desired resolution and speed of separation.

The preferred collection unit is an array of wells, each well capable of holding a fixed volume, e.g., ~1 µL, that is formed in a medium such as glass, plastic, polymer or gel plate. For example, an array plate with 5,400 wells per channel would be capable of collecting fractions for up to 1.5 hours with zone resolution of 1 sec. In general, the collection unit, preferably capable of collecting fractions having very small volumes, is constructed so as to maintain fraction solvent evaporation at a very low level. For separation methods that use an electric field, the fraction collection unit is in electrical contact with the separation channels. In addition, the collection unit is preferably biocompatible and disposable.

Figure 2:
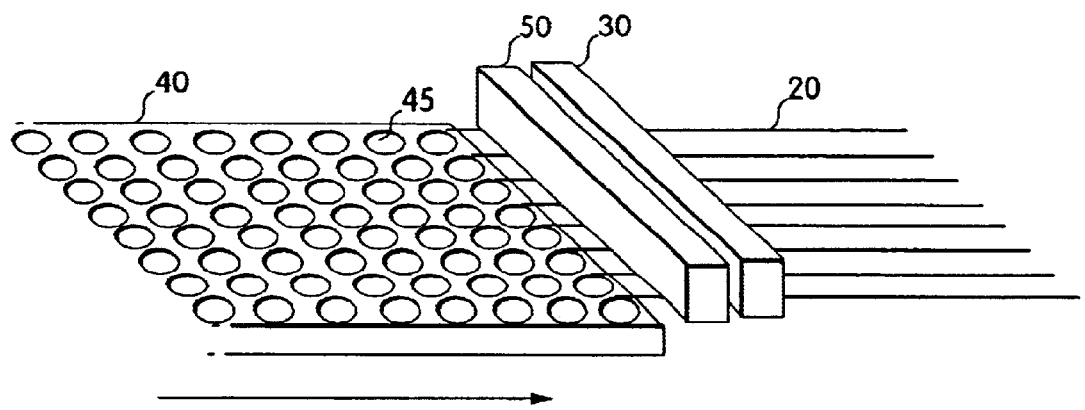
FIG. 2 shows another alternative embodiment of the micropreparative fraction collection system of the invention.

Two different detection systems are contemplated in the preferred system for identification of the desired fractions in the wells. In the first option, as shown in FIG. 2, an on-column detection unit (30), e.g., for laser induced fluorescence detection with a CCD camera or other image acquisition device, is positioned near the exit end of the individual capallaries in the separation capillary array (20). The signal from the detector is evaluated by a computer. Based on the known distances between the detection point and capillary exit, and the rate of fraction deposition into the array of wells in collection unit (40), the precise position of each collected fraction of interest in the multi-well plate can be determined.

Figure 3:
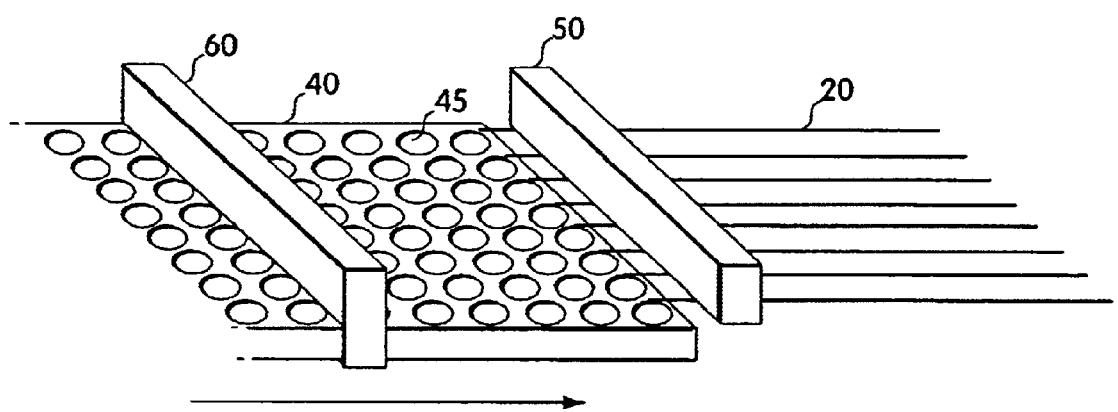
FIG. 3 shows another alternative embodiment of the micropreparative fraction collection system of the invention.

The second option, shown in FIG. 3, is based on post-collection scanning of the array well plate. In this configuration, a laser beam from an LIF scanner (60) scans rows of wells across the collection plate. Either real time scanning, in which the content of the deposited fractions is probed during the collection, or post run scanning can be used. After collection, fractions of interest can be transferred to a standard 96 or 384 well plate and amplified and sequenced using a robotic system and a DNA sequencer.

Figure 4:
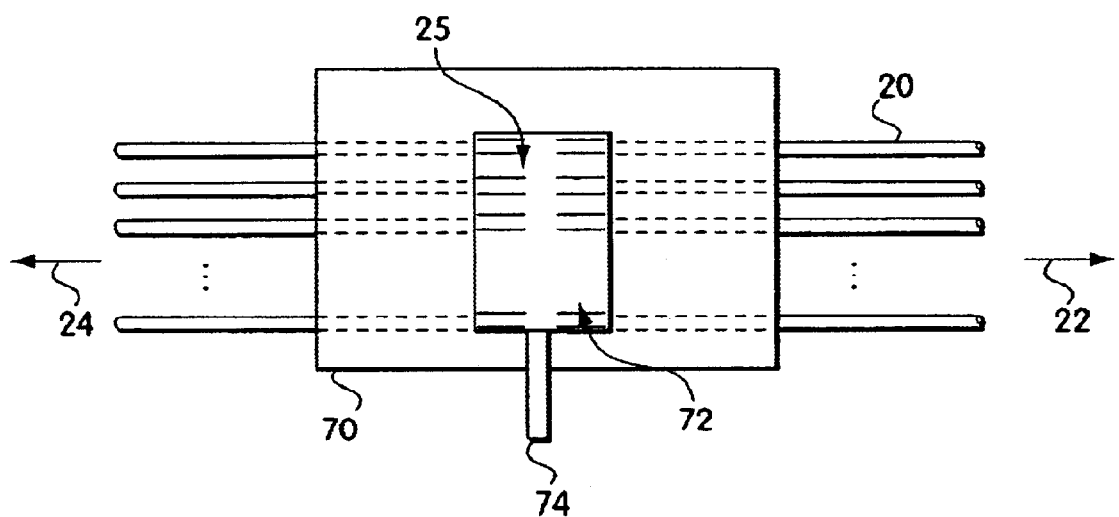
FIG. 4 shows a portion of a micropreparative fraction collection system according to the invention connected to a matrix replacement port.

For repetitive use of the capillary array, e.g., for CE, replacement of the separation matrix may be necessary. Referring to FIG. 4, the capillary array (20) may consist of two serial arrays (22, 24) aligned in a matrix replacement port (70). Replacement port (70) is a block of, e.g., glass or plastic having an internal cavity (72), where the ends of the capillaries in the two serial arrays are aligned at a narrow junction (25), which is filled with separation matrix. Separation matrix can be replaced as needed through an opening (74) in the matrix replacement port. During matrix replacement, positive pressure is applied to the matrix in junction (25) through the opening (74). Expelled matrix flows out from each end of all capillaries, and new matrix is introduced. After replacement, the matrix replacement port can be closed, the system reassembled and the next analysis commenced.

Figure 5:
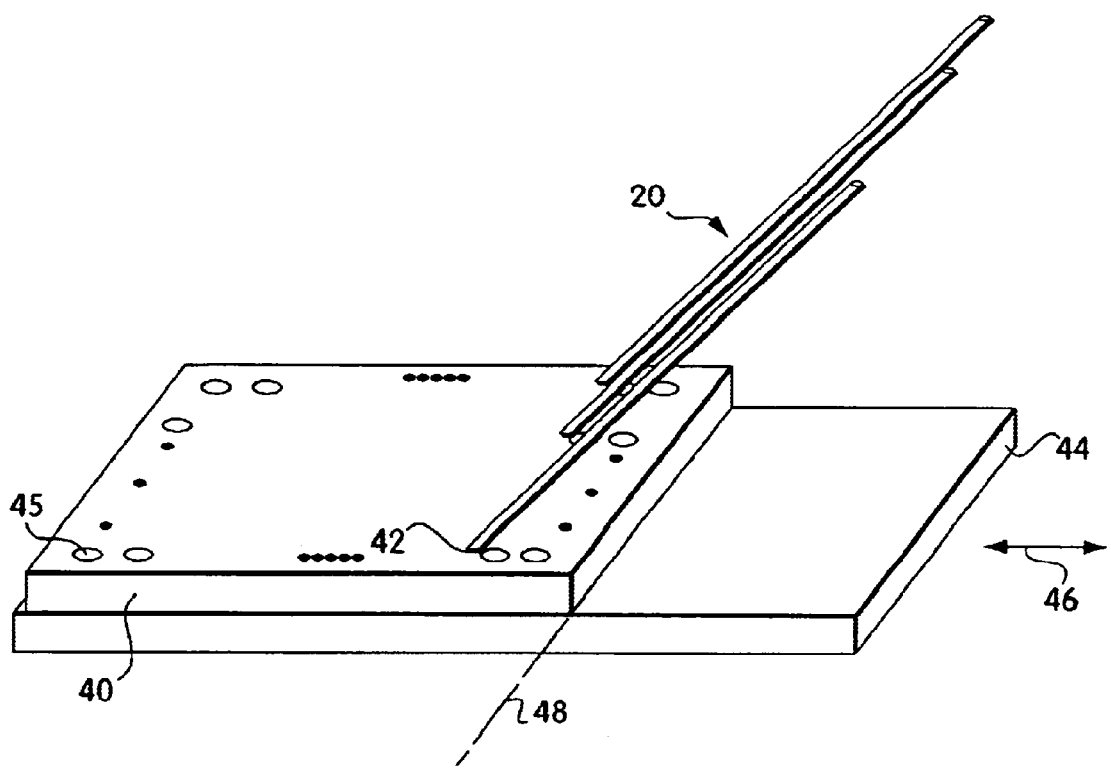
FIG. 5 shows a portion of a micropreparative fraction collection system according to the invention comprising a solvent permeable gel collection unit in contact with a separation capillary array.

For collection of the individual zones as they exit the separation capillaries, either a liquid sheath or electrokinetic means can be used for completion of the electrical circuit for those separation methods requiring a circuit. In the first case, as shown in FIGS. 2 and 3, the capillaries end in a sheath flow generator (50) and the sheath collection fluid, slowly flowing around the capillary ends, transports the material exiting the capillaries into individual wells (45) in the microtiter well plate collection unit (40). In the electrokinetic aided mode, as shown in FIG. 5, individual capillaries in separation capillary array (20) are in electrical contact (42) with the collection plate (40), and zones exiting the capillaries are deposited on the collection plate by electrokinetic transport (e.g., electrophoresis, electroosmosis). No sheath liquid is required in this mode of collection.

When very small sample volumes are being handled, there are serious issues, such as rapid solvent evaporation, for fraction collection unit design. Therefore, the preferred multi-well collection unit of the invention is constructed of an electrically conductive biocompatible, solvent permeable material such as agarose or polyacrylamide gel. Forms for collection gel plate casting can easily be made, either by regular machining or by micromachining technologies. The collection plates may contain a large number of structures for sample collection (wells, channels) and also for further sample handling—desalting, filtration, enzyme reactions, etc. Similar gel based plates can also be used for preseparation sample treatment, as a sample application unit (10) (see FIG. 1a) or as an independent unit for sample analysis. In this respect, the gel plate would be similar to standard micromachined devices, currently fabricated from glass, silicon or plastics. The advantages of the gel materials are that they are easily handled and molded to all types of desired configurations, they can reduce sample evaporation while also inhibiting sample diffusion or liquid leaking, and they can provide electrical conductivity, selective or complete ion permeability, and the possibility of creating devices with gradients of physico-chemical properties, egg., gradients of pore structure or pH.

Figure 6:
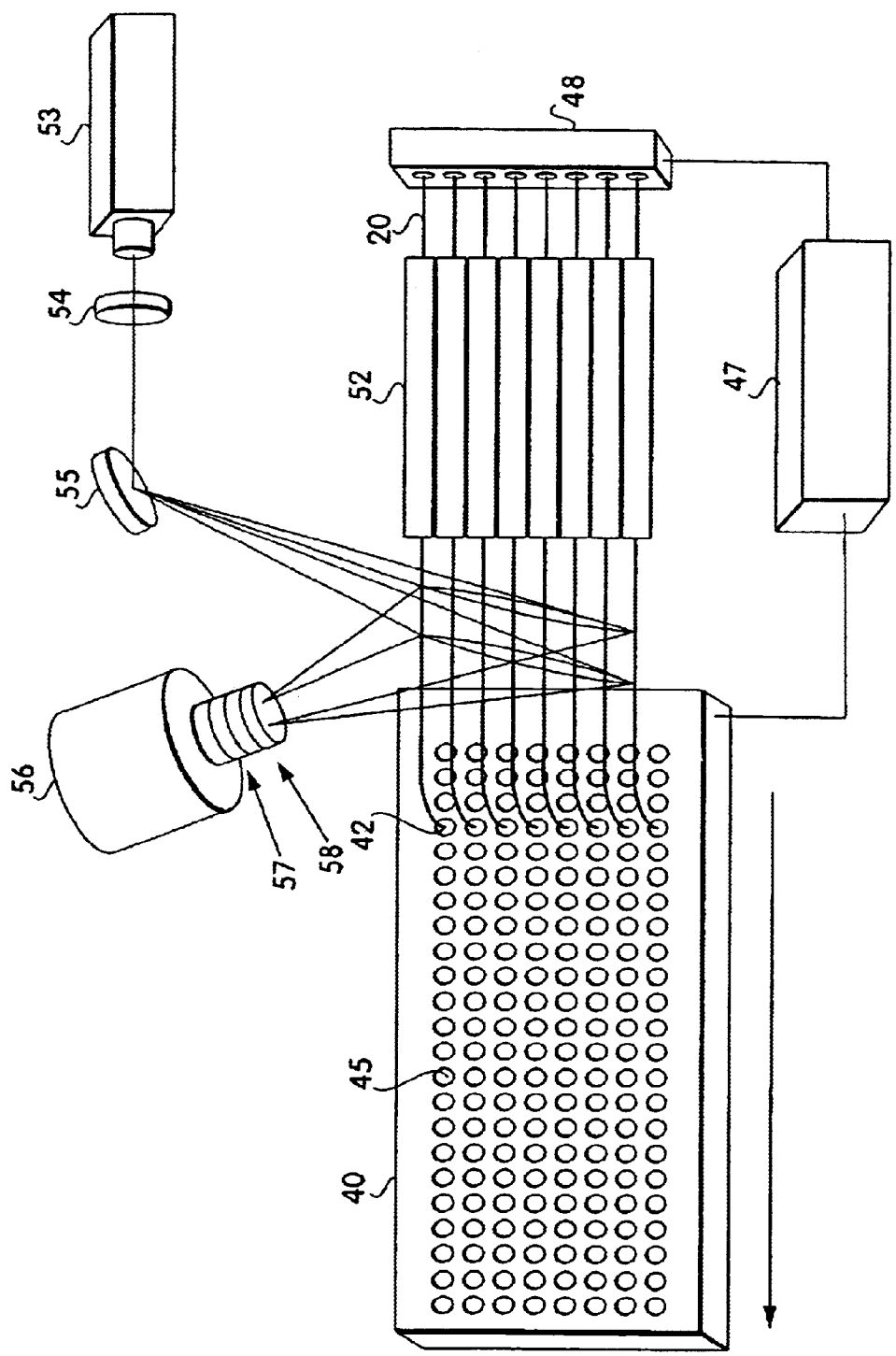
FIG. 6 shows an alternative embodiment of the micropreparative fraction collection system of the invention.

Examples of the system of the invention, including a gel based plate for collection of zones exiting the separation capillaries, are shown in FIGS. 5 and 6. The gel plate (40) has an array of collection wells (45). The plate is on a motorized stage (44), allowing its movement (46) relative to the capillary array (20). The ends of the separation capillaries (42) are in direct contact with the surface of the gel so that the uninterrupted electric current can be applied for the separation. Since the gel plate is electrically conductive, a single electrode (48) attached to the gel plate serves for electric connection of all the separation capillaries. Other features of a preferred system include a high voltage power source (47); a buffer reservoir (48); a solid state thermostat array (52), positioned to permit the control of capillary temperature during the separation process; and a laser illumination system (53), with associated line generator (54) and beam splitter (55). The laser system produces two point illumination for, e.g., laser induced fluorescence detection using a spectrograph/CCD detector (56), which can have associated lens (57) and notch filters (58).

The zones exiting the capillaries are collected into the micro-wells on the gel plate; the wells may contain a collection fluid. Once collected, the fractions in the wells can be transferred out of the wells or processed directly in the wells. The evaporation of the liquid from the wells, which is a major problem in handling of minute sample volumes, can be reduced or eliminated in this case since the gel itself contains a large excess of water. For especially small volumes, the gel plate is partially immersed in a solvent bath so that positive liquid flow into the gel and the wells of the gel will be maintained. Gel plates could be cast with microchannels, allowing consecutive microfluidic sample handling. These plates may also be used to perform two dimensional electrophoresis or be utilized as a micro-storage device.

Beyond the use described above as a material from which microtiter plates can be made, solvent permeable, e.g., hydrophilic, gels are useful in many different ways, such as for fabrication of miniaturized devices for sample treatment, reaction and analysis. Microfabricated analytical devices are currently produced from standard solid materials such as glass, certain metals, silicon, silicon resins and other plastic materials. These materials are generally rigid and impermeable to both ions and water. Electric conductivity is provided only when metal or semiconductor materials are used. While the above mentioned materials can be used for fabrication of very small features such as channels for sample delivery and separation, sample inlet and outlet ports, unions, etc., some other desirable features such as permeability for water or selective permeability for ionic species and/or a low absorptivity surface cannot easily be achieved in prior art devices. Miniaturized devices fabricated of the solvent permeable gel material of the invention can contain all the desirable features of the devices of the prior art and in addition solve the problem of rapid evaporation of samples.

Figure 7A:
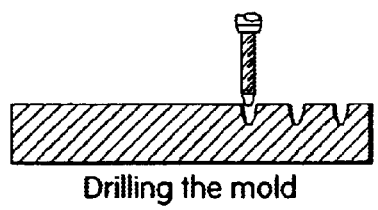
FIGS. 7A–7E show a scheme for preparing a solvent permeable gel collection unit for use in the micropreparative fraction collection system of the invention.
Figure 7B:
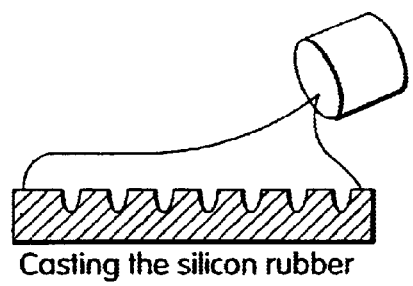
Figure 7C:
Figure 7D:
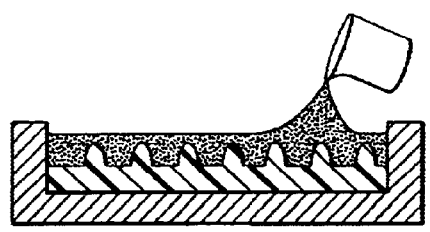
Figure 7E:

A miniaturized analogue of the microtiter well plate can easily be produced by gel casting into any desired shape. Referring to FIGS. 7A–7E, by using the procedures of drilling a mold (FIG. 7A), casting, e.g., silicon rubber (FIG. 7B) to prepare a silicon negative (FIG. 7C), placing the negative in a mold and and casting the polymer solution (FIG. 7D), thousands of nano-wells (submicroliter volume) can be produced in a small gel plate (FIG. 7E) for handling of submicroliter sample volumes. In use, a nano-well gel plate, such as that of FIG. 7E, is partially immersed in a buffer solution. In spite of the extremely small volumes deposited, evaporation is compensated for by water supplied by liquid flow into and through the surrounding gel matrix.

Figure 8A:
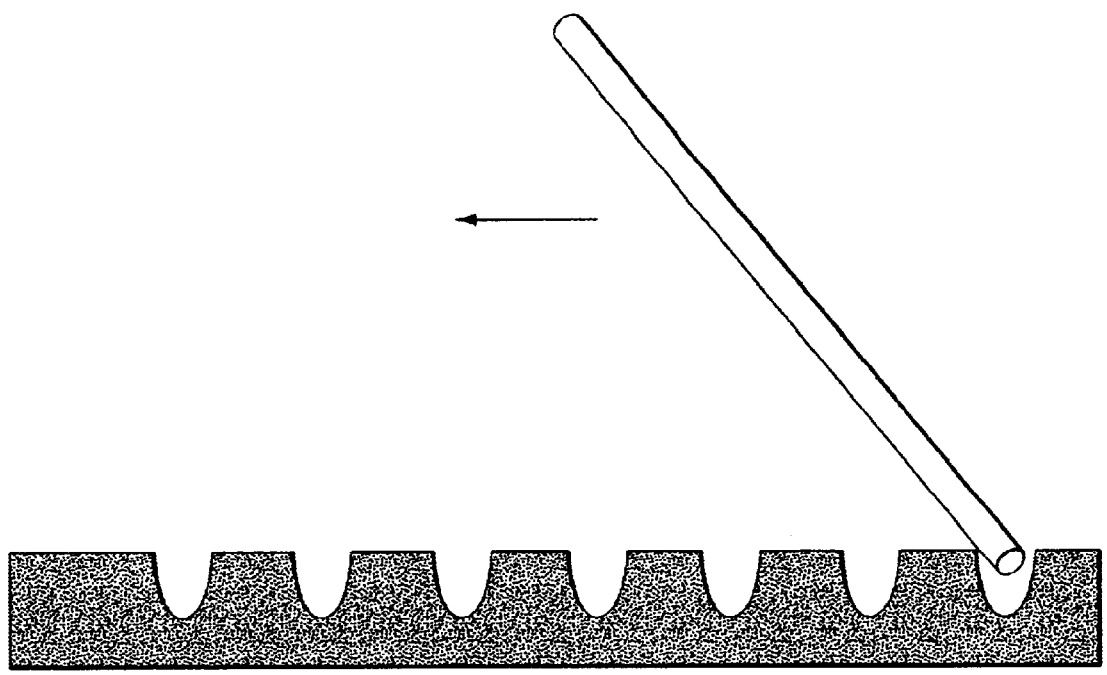
FIGS. 8A and 8B show two possible orientations of a separation capillary with respect to a well of a multi-well collection unit in the micropreparative fraction collection system of the invention.
Figure 8B:
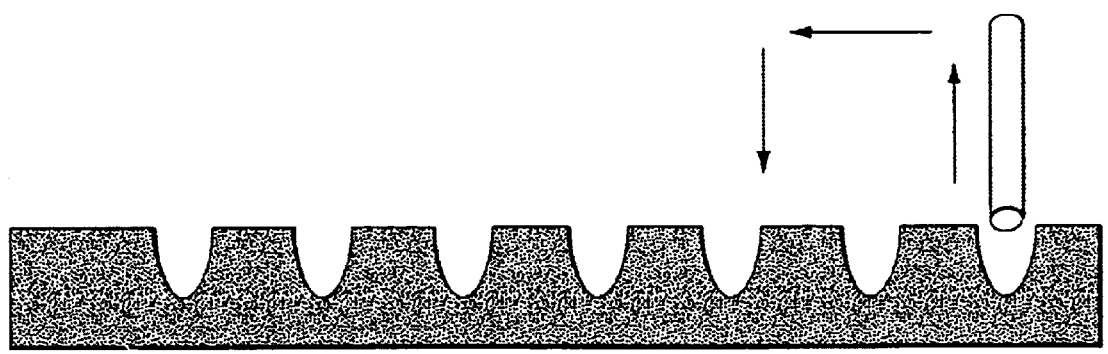
Figure 10A:
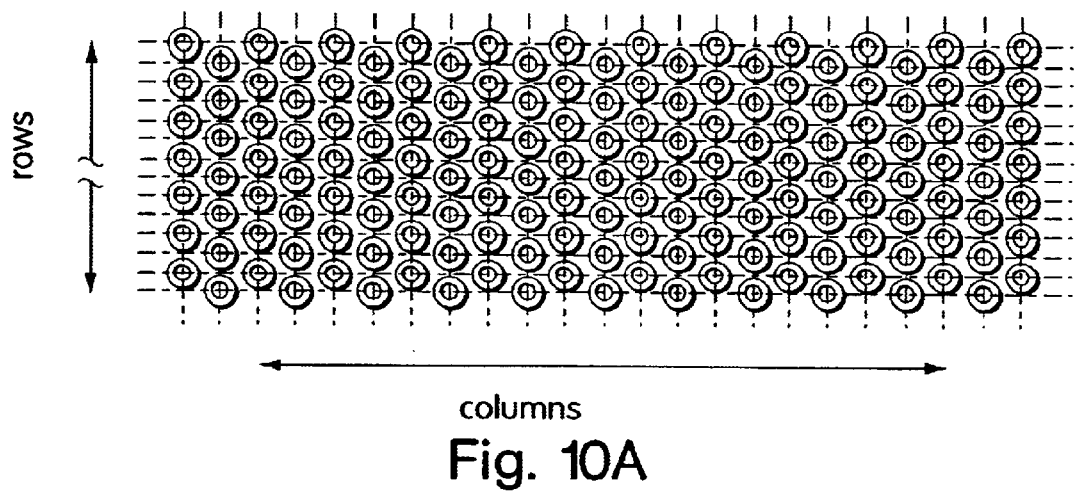
FIGS. 10A–10D show a top view, side view and spacing of individual wells of the alternative well configuration of FIG. 9B.
Figure 10B:
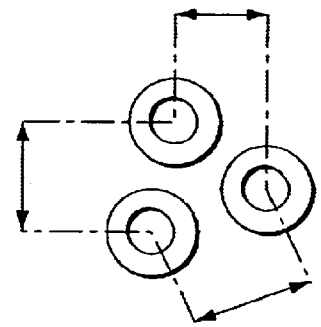
Figure 10C:
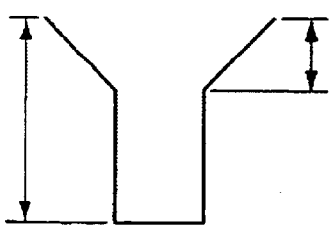
Figure 10D:

The angle of capillary exit end orientation in relation to the opening of individual wells is an important parameter for ease of sample collection. Orientation at an angle, as shown in FIG. 8A, allows continuous electrical contact to be maintained with the gel surface surrounding traditionally shaped wells. (Refer also to FIG. 9A.) A capillary with a vertically oriented tip, as shown in FIG. 8B, can be positioned more precisely and can be moved in any direction; however, when a vertically oriented capillary tip is moved from one traditionally shaped well to another, the electrical contact with the surface of the gel is often broken. To address this problem, we have designed "nozzle" shaped wells, as shown in FIG. 9B and FIGS. 10A–10D. In this configuration, the outer top edges of the individual wells are particularly close together; a vertically oriented capillary tip can simply be pushed through the fluid gel from one well to another, under the surface of the buffer, maintaining the electrical connection.

Since the properties of the gel can easily be modified by changing gel concentration, crosslinking or chemically modifiying the gel, functions difficult to incorporate with standard materials may be possible. For example, electrophoretic separation can be performed in a gel with an array of wells and the separated substances can easily be removed from the wells without tedious extraction from the gel. Pore and/or pH gradient gels would be especially beneficial for this application, e.g., for protein preparation. For example, Immobilin™ can be used as a gel matrix for micropreparative isoelectric focusing. Of course, other functionalized gels may be used. For example, immobilized antibody or antigen containing gels may be used for affinity capture. Since channels and wells of practically any shape can be easily fabricated by gel casting, many structures fabricated in "classical chips" can be fabricated in gel more cost effectively. In addition, enzymes can be immobilized in the gel structure, and reactions such as digestion (protein or DNA), PCR and sequencing can be carried out. The gel can be heated, e.g., by microwaves, if necessary. If the enzymes (substrates, template, . . .) are immobilized in the gel, little or no sample cleanup would be necessary compared to other sample handling systems. ssDNA can be fixed in the gel for specific hybridization to a complementary DNA strand. In addition, other biospecific groups such as antibodies could also be immobilized in individual wells. In particular, inert particles, such as beads, can be placed in individual wells, as carriers of active materials, e.g., antibldies, enzymes, substrates, etc. For, example, functionalized solid phase particles would be useful for on-plate combinatorial chemical analysis.

Besides bare gel blocks casted or molded for the purposes described above, other contemplated uses for hydrophilic gels are as components of "cassettes." Such cassettes could be hybrid gel-plastic or gel-glass or gel-metal devices or chips, where a mold serves as a gel plate enclosure. All surfaces of the gel block would be covered, besides channels and wells. This design would both prevent excessive losses of water from the gel during sample manipulation (e.g., microwave heating) and ease the handling of the gel devices. A mold would be made as a reusable device, which would significantly reduce costs, especially if the mold contains embedded contacts or heating elements.

The following example is presented to illustrate the advantages of the present invention and to assist one of ordinary skill in making and using the same. These examples are not intended in any way otherwise to limit the scope of the disclosure.

EXAMPLE

Figure 11:
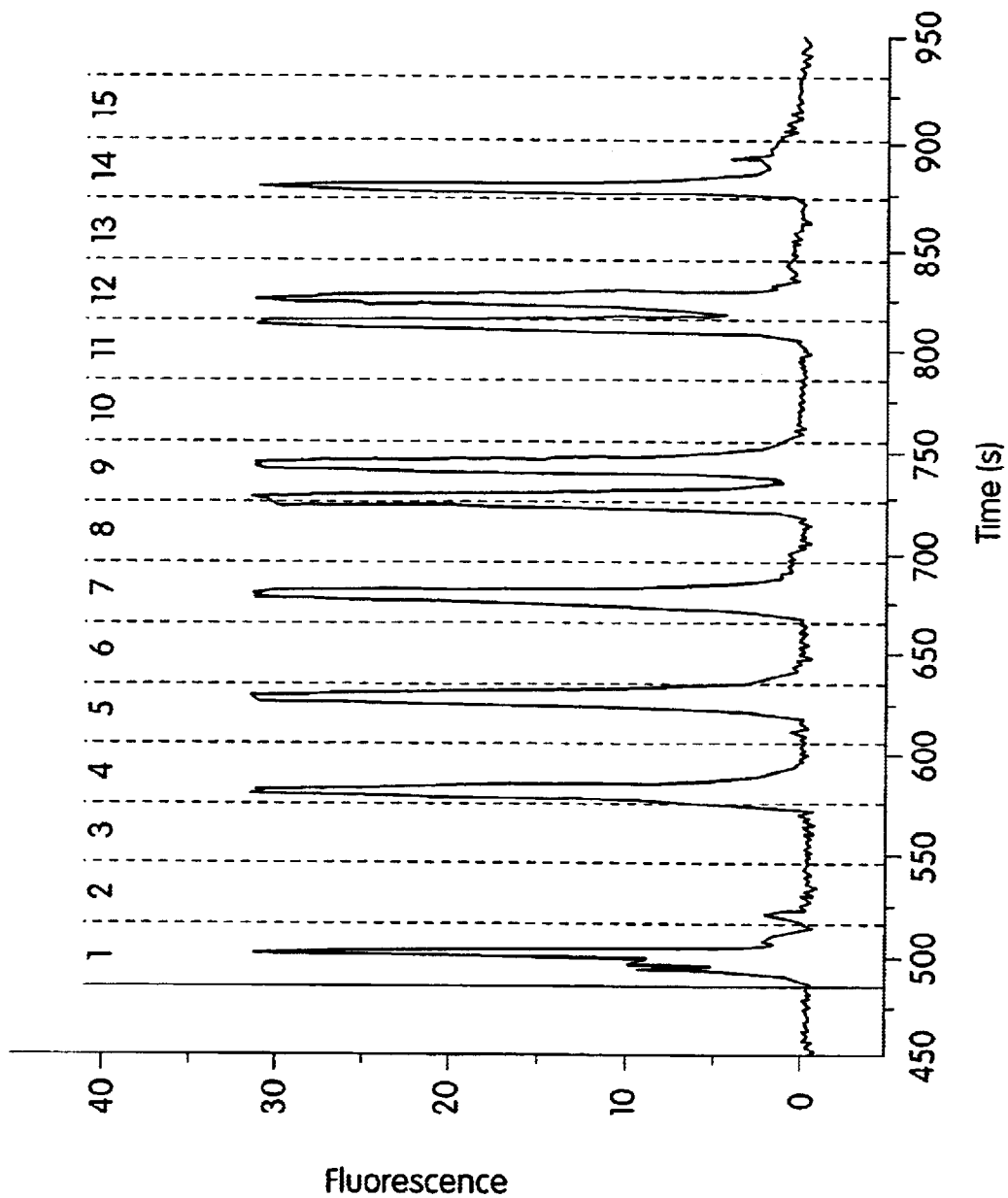
FIG. 11 is a graph showing real time on-column detection of a sample fractionated using the system of the invention.
Figure 12B:
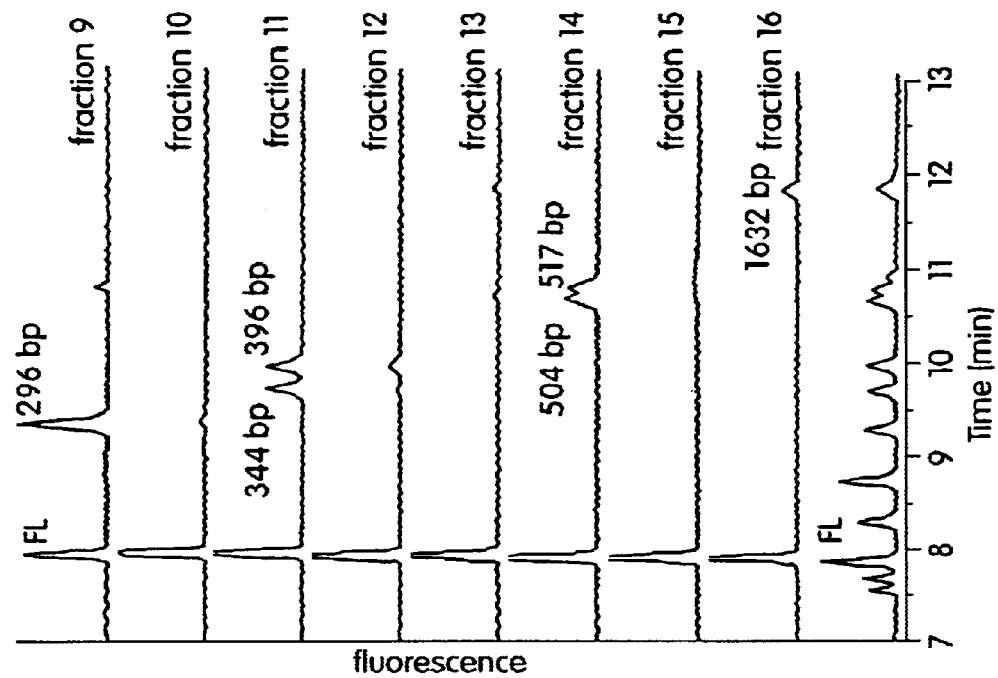
FIGS. 12A and 12B are individual fraction profiles of fractions collected from the column of FIG. 11.
Figure 12A:
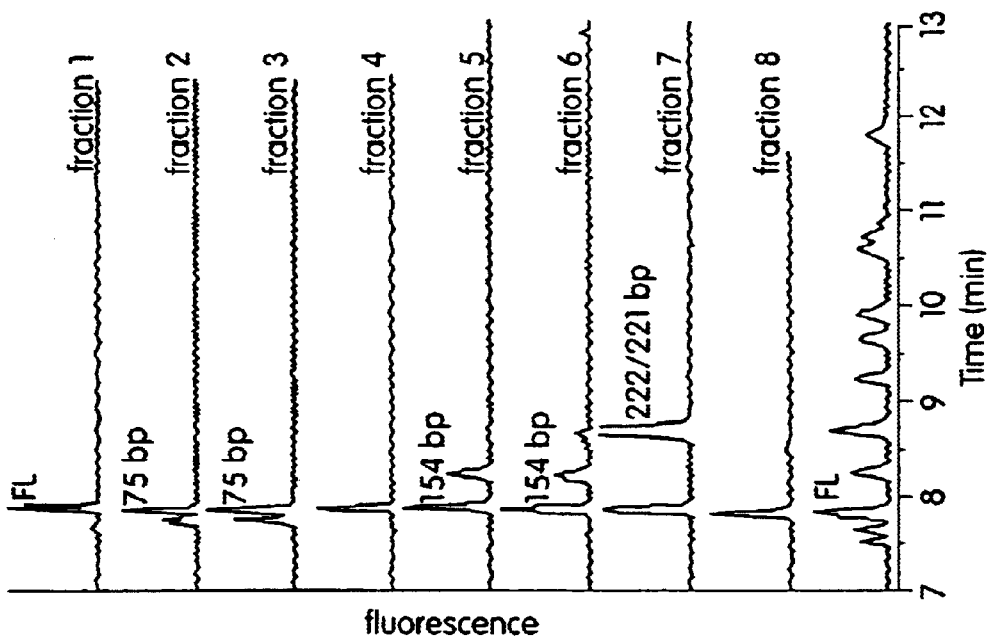
Figure 13:
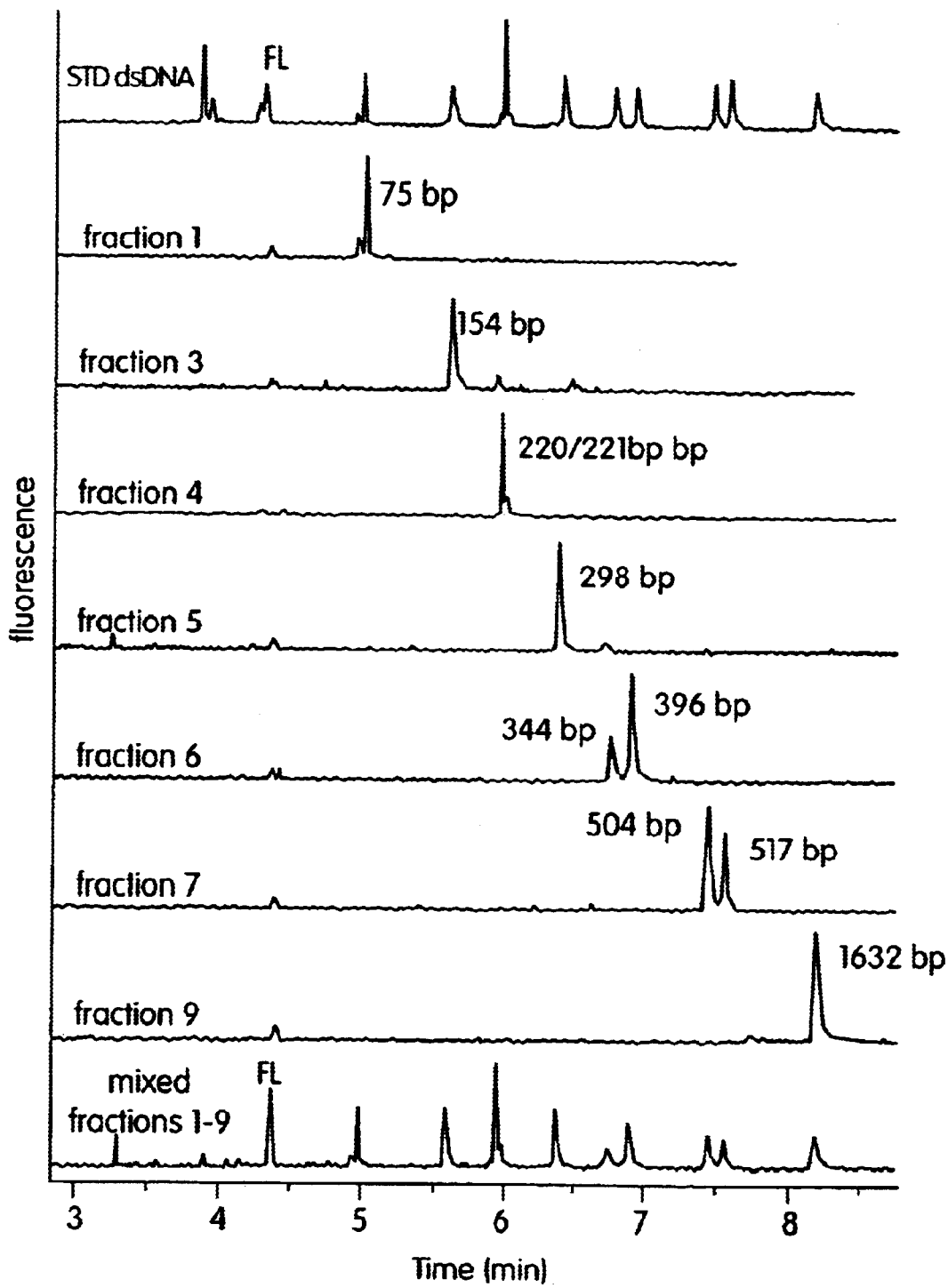
FIG. 13 shows on-column detection, individual fraction profiles and a profile of pooled fractions from the analysis of another sample using the system of the invention.

To verify that individual components of a sample can be collected using the system of the invention with a microtiter multi-well collection plate, an experiment was conducted with a fluorescently labelled double stranded DNA restriction fragment mixture (commercially available as pBR322/Hinf I) as a sample. The mixture was separated by capillary electrophoresis (CE) in a 75 μm i.d. polyvinylalcohol coated fused silica capillary filled with linear polyacrylamide (4% solution in 50 mM Tris/TAPS buffer) in an electric field of 370 V/cm. The total capillary length was 27 cm and the length from injection to detection point was 25 cm. Injection was performed electrokinetically for 2–3 seconds at 370 V/cm. Detection was accomplished on-column by laser induced fluorescence using an argon ion laser (488 nm) and emission at 520 nm by means of confocal detection. The microtiter gel collection plate was a 3% agarose composite (a mixture of 1.5% large pore and 1.5% narrow pore agarose material), containing a single lane of microwells. During separation, the capillary was moved from one microwell to another in constant time intervals of 30 seconds. After deposition, the fractions were transferred out of the microwells, desalted and identified by re-injection and capillary electrophoresis. FIG. 11 shows the detector signal during the original separation analysis of the collected fractions. The 30 second collection time intervals are depicted as vertical lines, with the fractions labelled from 1 to 15. FIG. 12 shows the results after re-injection of all the collected fractions (fraction 1 through 8 in FIG. 12A and fractions 9 through 16 in FIG. 12B). The results clearly show individually collected fractions with no contamination between fractions. The final profile depicted at the end of each of FIGS. 12A and 12B shows that the pooled fractions contain all of the components of the individual fractions. FIG. 13 shows another successful fraction collection experiment from a different sample.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A micropreparative fraction collection system comprising
   a separation unit comprising two or more essentially parallel capillary separation columns, wherein said capillary separation columns comprise channels on a microfabricated device; and
   a fraction collection unit, wherein said fraction collection unit is configured, and said separation unit is oriented, so as to cause simultaneous collection of fractions directly from said capillary separation columns into said fraction collection unit.

2. A micropreparative fraction collection system comprising
   a separation unit comprising two or more essentially parallel capillary separation columns;
   a fraction collection unit, wherein said fraction collection unit is configured, and said separation unit is oriented, so as to cause simultaneous collection of fractions directly from said capillary separation columns into said fraction collection unit; and
   a detection unit, wherein said detection unit is positioned for post-column scanning of collected fractions in said fraction collection unit.

3. A micropreparative fraction collection system comprising
   a separation unit comprising two or more essentially parallel capillary separation columns; and
   a fraction collection unit, wherein said fraction collection unit is configured, and said separation unit is oriented, so as to cause simultaneous collection of fractions directly from said capillary separation columns into said fraction collection unit, and wherein, further, said fraction collection unit comprises a solvent permeable gel.

4. A micropreparative fraction collection system comprising
   a separation unit comprising two or more essentially parallel capillary separation columns; and
   a fraction collection unit, wherein said fraction collection unit is configured, and said separation unit is oriented, so as to cause simultaneous collection of fractions directly from said capillary separation columns into said fraction collection unit, and wherein, further, said fraction collection unit comprises an electrically conductive gel.

5. A micropreparative fraction collection system comprising
   a separation unit comprising two or more essentially parallel capillary separation columns; and
   a fraction collection unit, wherein said fraction collection unit is configured, and said separation unit is oriented, so as to cause simultaneous collection of fractions directly from said capillary separation columns into said fraction collection unit, and wherein, further, said fraction collection unit comprises a biocompatible gel.

6. A micropreparative fraction collection system comprising
   a separation unit comprising two or more essentially parallel capillary separation columns; and a fraction collection unit, wherein said fraction collection unit is configured, and said separation unit is oriented, so as to cause simultaneous collection of fractions directly from said capillary separation columns into said fraction collection unit, wherein said fraction collection unit is electrically conductive and wherein, further, said system is lacking a sheath flow generator and said fraction collection unit is configured, and said separation unit is oriented, so as to cause simultaneous collection of fractions directly from said capillary separation columns into said fraction collection unit without the use of a sheath flow liquid.

7. The micropreparative fraction collection system of claim 6, wherein said fraction collection unit comprises an electrically conductive gel or an electrically conductive plastic.

8. A micropreparative fraction collection system comprising a separation unit comprising two or more essentially parallel capillary separation columns;

a fraction collection unit, wherein said fraction collection unit is configured, and said separation unit is oriented, so as to cause simultaneous collection of fractions directly from said capillary separation columns into said fraction collection unit; and a separation medium replacement unit.

9. The micropreparative fraction collection system of claim 8, wherein said separation medium is a separation matrix.

* * * * *

UNITED STATES PATENT AND TRADEMARK OFFICE
CERTIFICATE OF CORRECTION

PATENT NO. : 6,660,149 B1 Page 1 of 1
APPLICATION NO. : 09/530118
DATED : December 9, 2003
INVENTOR(S) : Barry L. Karger et al.

It is certified that error appears in the above-identified patent and that said Letters Patent is hereby corrected as shown below:

On the title page, item (73) Assignee, "Beckman Coulter, Inc. Fullerton, CA (US)" should read --Northeastern University, Boston, MA (US)--;

On the title page, item (74) Attorney, Agent, or Firm, "William H. May; D. David Hill; Weingarten, Schurgin, Gagnebin & Lebovici LLP" should read --Weingarten, Schurgin, Gagnebin & Lebovici LLP--;

Column 3, line 60, "chins." should read --chips.--; and

Column 5, line 26, "egg.," should read --e.g.,--.

Signed and Sealed this

Third Day of June, 2008

JON W. DUDAS
*Director of the United States Patent and Trademark Office*